(12) United States Patent
Wang

(10) Patent No.: US 6,290,485 B1
(45) Date of Patent: Sep. 18, 2001

(54) MOLD FOR FORMING A BALLOON CATHETER HAVING STEPPED COMPLIANCE CURVE

(76) Inventor: Lixiao Wang, 12822-86th Place North, Maple Grove, MN (US) 55369

( * ) Notice: Subject to any disclaimer, the term of this patent is extended or adjusted under 35 U.S.C. 154(b) by 0 days.

(21) Appl. No.: 09/396,841

(22) Filed: Sep. 15, 1999

Related U.S. Application Data (60) Continuation of application No. 08/931,190, filed on Sep. 16, 1997, now Pat. No. 5,980,532, which is a division of application No. 08/397,615, filed on Mar. 2, 1995, now Pat. No. 5,749,851.

(51) Int. Cl.[7] ............................. B29D 23/00; B29C 33/42
(52) U.S. Cl. ......................... 425/470; 264/573; 425/522
(58) Field of Search ........................ 264/573; 425/403, 425/522, 470

(56) References Cited

U.S. PATENT DOCUMENTS

| | | | |
|---|---|---|---|
| 4,130,617 | * 12/1978 | Wallace | .............................. 425/529 |
| 4,490,421 | * 12/1984 | Levy | .................................... 264/573 |
| 4,580,568 | 4/1986 | Gianturco . | |
| 4,649,922 | 3/1987 | Wiktor . | |
| 4,655,771 | 4/1987 | Wallsten . | |
| 4,681,110 | 7/1987 | Wiktor . | |
| 4,705,517 | 11/1987 | DiPisa, Jr. . | |
| 4,733,665 | 3/1988 | Palmaz . | |
| 4,740,207 | 4/1988 | Kreamer . | |
| 4,744,366 | 5/1988 | Jang . | |
| 4,760,849 | 8/1988 | Kropf . | |
| 4,763,654 | 8/1988 | Jang . | |
| 4,776,337 | 10/1988 | Palmaz . | |
| 4,777,951 | 10/1988 | Cribier et al. | ....................... 128/344 |
| 4,795,458 | 1/1989 | Regan . | |
| 4,800,882 | 1/1989 | Gianturco . | |
| 4,830,003 | 5/1989 | Wolff et al. . | |
| 4,856,516 | 8/1989 | Hillstead . | |
| 4,877,030 | 10/1989 | Beck et al. . | |
| 4,878,906 | 11/1989 | Lindemann et al. . | |
| 4,886,062 | 12/1989 | Wiktor . | |
| 4,896,670 | 1/1990 | Crittenden | ............................ 606/194 |
| 4,907,336 | 3/1990 | Gianturco . | |
| 4,913,141 | 4/1990 | Hillstead . | |
| 4,921,483 | 5/1990 | Wijay et al. . | |
| 4,922,905 | 5/1990 | Stecker . | |
| 4,923,464 | 5/1990 | DiPisa, Jr. . | |
| 4,932,956 | 6/1990 | Reddy et al. . | |

(List continued on next page.)

FOREIGN PATENT DOCUMENTS

| | | |
|---|---|---|
| 197 787 | 10/1986 | (EP) . |
| 540 858 | 5/1993 | (EP) . |
| 582 870 | 2/1994 | (EP) . |
| 0 669 143 A1 | 8/1995 | (EP) . |
| 0 745 395 A2 | 12/1996 | (EP) . |
| 94/02193 | 2/1994 | (WO) . |

Primary Examiner—Robert Davis (57) ABSTRACT

A method for installing a stent in a vessel utilizes a single balloon catheter for both low pressure predilation at a relatively small diameter to open the lesion sufficiently to allow insertion and deployment of the stent across the lesion and for subsequent high pressure embedding of the stent in the vessel wall. The same balloon catheter may also be employed to insert and deploy the stent. The balloons utilized in the method have a stepped compliance curve which allows for predilation at a low pressure and predetermined diameter and for high pressure embedding at a substantially larger diameter. The balloons may be provided with a configuration in which only a portion of the balloon has a stepped compliance curve while a further portion has a generally linear compliance profile. With such balloons high pressure treatment of the vessel wall areas not reinforced by the stent can be avoided despite the occurence of longitudinal shrinkage of the stent during expansion thereof.

2 Claims, 5 Drawing Sheets

U.S. PATENT DOCUMENTS

| | | | |
|---|---|---|---|
| 4,954,126 | 9/1990 | Wallstén . | |
| 4,958,634 | 9/1990 | Jang . | |
| 4,969,458 | 11/1990 | Wiktor . | |
| 4,969,890 | 11/1990 | Sugita et al. . | |
| 4,990,151 | 2/1991 | Wallstén . | |
| 4,990,155 | 2/1991 | Wilkoff . | |
| 4,994,071 | 2/1991 | MacGregor . | |
| 5,007,926 | 4/1991 | Derbyshire . | |
| 5,017,325 | 5/1991 | Jackowski et al. | 264/521 |
| 5,019,085 | 5/1991 | Hillstead . | |
| 5,019,090 | 5/1991 | Pinchuk . | |
| 5,035,706 | 7/1991 | Gianturco et al. . | |
| 5,041,089 | 8/1991 | Mueller et al. | 604/96 |
| 5,041,125 * | 8/1991 | Montano, Jr. | 606/192 |
| 5,041,126 | 8/1991 | Gianturco . | |
| 5,049,131 | 9/1991 | Deuss | 604/96 |
| 5,049,132 | 9/1991 | Shaffer et al. | 604/101 |
| 5,055,024 * | 10/1991 | Jackowski et al. | 425/530 |
| 5,059,211 | 10/1991 | Stack et al. . | |
| 5,061,275 | 10/1991 | Wallstén et al. . | |
| 5,064,435 | 11/1991 | Porter . | |
| 5,071,406 | 12/1991 | Jang | 604/96 |
| 5,074,845 | 12/1991 | Miraki et al. | 604/101 |
| 5,078,726 | 1/1992 | Kreamer . | |
| 5,089,006 | 2/1992 | Stiles . | |
| 5,092,841 | 3/1992 | Spears . | |
| 5,092,877 | 3/1992 | Pinchuk . | |
| 5,104,399 | 4/1992 | Lazarus . | |
| 5,104,404 | 4/1992 | Wolff . | |
| 5,108,416 | 4/1992 | Ryan et al. . | |
| 5,108,417 | 4/1992 | Sawyer . | |
| 5,116,309 | 5/1992 | Coll . | |
| 5,116,318 | 5/1992 | Hillstead . | |
| 5,116,360 | 5/1992 | Pinchuk et al. . | |
| 5,116,365 | 5/1992 | Hillstead . | |
| 5,122,154 | 6/1992 | Rhodes . | |
| 5,123,917 | 6/1992 | Lee . | |
| 5,133,732 | 7/1992 | Wiktor . | |
| 5,135,536 | 8/1992 | Hillstead . | |
| 5,147,385 | 9/1992 | Beck et al. . | |
| 5,163,952 | 11/1992 | Froix . | |
| 5,171,262 | 12/1992 | MacGregor . | |
| 5,192,297 | 3/1993 | Hull . | |
| 5,195,984 | 3/1993 | Schatz . | |
| 5,207,695 | 5/1993 | Trout, III | 606/153 |
| 5,234,457 | 8/1993 | Andersen . | |
| 5,282,824 | 2/1994 | Gianturco . | |
| 5,290,306 | 3/1994 | Trotta et al. . | |
| 5,292,331 | 3/1994 | Boneau . | |
| 5,304,340 * | 4/1994 | Downey | 264/573 |
| 5,320,605 | 6/1994 | Sahota | 604/101 |
| 5,338,298 | 8/1994 | McIntyre | 604/96 |
| 5,348,538 | 9/1994 | Wang et al. . | |
| 5,352,199 | 10/1994 | Tower | 604/96 |
| 5,358,487 | 10/1994 | Miller . | |
| 5,403,340 | 4/1995 | Wang et al. . | |
| 5,409,495 | 4/1995 | Osborn . | |
| 5,411,477 * | 5/1995 | Saab | 425/526 |
| 5,415,635 | 5/1995 | Bagaoisan et al. . | |
| 5,437,632 | 8/1995 | Engelson | 604/96 |
| 5,447,497 | 9/1995 | Sogard et al. | 604/101 |
| 5,460,610 | 10/1995 | Don Michael | 604/101 |
| 5,470,313 | 11/1995 | Crocker et al. . | |
| 5,478,349 | 12/1995 | Nicholas | 606/198 |
| 5,490,838 | 2/1996 | Miller . | |
| 5,500,181 | 3/1996 | Wang et al. . | |
| 5,545,134 | 8/1996 | Hilaire et al. | 604/96 |
| 5,549,551 | 8/1996 | Peacock, III et al. | 604/96 |
| 5,556,383 | 9/1996 | Wang et al. | 604/96 |
| 5,567,203 | 10/1996 | Euteneuer et al. | 604/96 |
| 5,567,720 | 10/1996 | Averback | 514/345 |
| 5,609,605 | 3/1997 | Marshall et al. | 606/191 |
| 5,613,980 | 3/1997 | Chauhan | 606/194 |
| 5,640,560 | 6/1997 | Smith | 395/615 |
| 5,645,560 | 7/1997 | Crocker et al. | 606/192 |
| 5,645,789 | 7/1997 | Roucher et al. | 264/529 |
| 5,647,848 | 7/1997 | Jørgensen | 604/96 |
| 5,695,498 | 12/1997 | Tower | 606/108 |
| 5,749,851 | 5/1998 | Wang | 604/96 |
| 5,800,521 | 9/1998 | Orth | 623/1 |
| 5,843,116 | 12/1998 | Crocker et al. | 606/192 |
| 5,980,532 | 11/1999 | Wang | 606/108 |

* cited by examiner

MOLD FOR FORMING A BALLOON CATHETER HAVING STEPPED COMPLIANCE CURVE

This is a continuation application of copending application 08/931,190, filed Sep. 16, 1997, now U.S. Pat. No. 5,980,532, which is a division of application 08/397,615, filed Mar. 2, 1995, now U.S. Pat. No. 5,749,851.

BACKGROUND OF THE INVENTION

The present invention relates generally to a method of installing a stent utilizing a balloon catheter to perform an initial angioplasty and to seat the stent after it has been located in the vessel. The invention also relates to novel balloon structures which have particular use in the method of the invention.

Angioplasty, an accepted and well known medical practice involves inserting a balloon catheter into the blood vessel of a patient, maneuvering and steering the catheter through the patient's vessels to the site of the lesion with the balloon in an uninflated form. The uninflated balloon portion of the catheter is located within the blood vessel such that it crosses the lesion or reduced area. Pressurized inflation fluid is metered to the inflatable balloon through a lumen formed in the catheter to thus dilate the restricted area. The inflation fluid is generally a liquid and is applied at relatively high pressures, usually in the area of six to twenty atmospheres. As the balloon is inflated it expands and forces open the previously closed area of the blood vessel. Balloons used in angioplasty procedures such as this are generally fabricated by molding and have predetermined design dimensions such as length, wall thickness and nominal diameter. Balloon catheters are also used in other systems of the body for example the prostate and the urethra. Balloon catheters come in a large range of sizes and must be suitably dimensioned for their intended use.

Recently the use of a catheter delivered stent to prevent an opened lesion from reclosing or to reinforce a weakened vessel segment, such as an aneurism, has become a common procedure. A typical procedure for stent installation involves performing an initial angioplasty to open the vessel to a predetermined diameter sufficient to permit passage of a stent delivery catheter across the lesion, removal of the angioplasty balloon catheter, insertion of a delivery catheter carrying the stent and a stent deploying mechanism, deploying the stent across the opened lesion so as to seperate the stent from the catheter and bring it into contact with the vessel wall, usually with dilation to a larger diameter using a balloon larger than the balloon of the predilation catheter, and then removing the delivery catheter (after deflating the balloon if used). In many cases it has become the practice to then "retouch" the dilation by deploying a third catheter carrying a balloon capable of dilating at a substantially higher pressure to drive the stent into the vessel wall, thereby to assure that there is no risk of the stent later shifting its position and to reduce occurance of restenosis or thrombus formation. This third "retouch" dilation is often considered necessary when the balloon used to seat the stent is made of a compliant material because such balloons generally cannot be safely pressurized above 9–12 atm., and higher pressures are generally considered necessary to assure full uniform lesion dilation and seating of the stent.

A wide variety of stent configurations and deployment methods are known. For instance, stent configurations include various forms of bent wire devices, self-expanding stents; stents which unroll from a wrapped configuration on the catheter; and stents which are made of a deformable material so that the device may be deformed on deployment from a small diameter to a larger diameter configuration. References disclosing stent devices and deployment catheters include:

| | |
|---|---|
| U.S. Pat. No. 4733665 Palmaz | U.S. Pat. No. 4681110 Wiktor |
| U.S. Pat. No. 4776337 Palmaz | U.S. Pat. No. 4800882 Gianturco |
| U.S. Pat. No. 5195894 Schatz | U.S. Pat. No. 4830003 Wolff et al |
| U.S. Pat. No. 5234457 Anderen | U.S. Pat. No. 4856516 Hillstead |
| U.S. Pat. No. 5116360 Pinchuck et al | U.S. Pat. No. 4922905 Strecker |
| U.S. Pat. No. 5116318 Hillstead | U.S. Pat. No. 4886062 Wiktor |
| U.S. Pat. No. 4649922 Wiktor | U.S. Pat. No. 4907336 Gianturco |
| U.S. Pat. No. 4655771 Wallsten | U.S. Pat. No. 4913141 Hillstead |
| U.S. Pat. No. 5089006 Stiles | U.S. Pat. No. 5092877 Pinchuk |
| U.S. Pat. No. 5007926 Derbyshire | U.S. Pat. No. 5123917 Lee |
| U.S. Pat. No. 4705517 DiPisa, Jr. | U.S. Pat. No. 5116309 Coll |
| U.S. Pat. No. 4740207 Kreamer | U.S. Pat. No. 5122154 Rhodes |
| U.S. Pat. No. 4877030 Beck et al | U.S. Pat. No. 5133732 Wiktor |
| U.S. Pat. No. 5108417 Sawyer | U.S. Pat. No. 5135536 Hillstead |
| U.S. Pat. No. 4923464 DiPisa, Jr. | U.S. Pat. No. 5282824 Gianturco |
| U.S. Pat. No. 5078726 Kreamer | U.S. Pat. No. 5292331 Boneau |
| U.S. Pat. No. 5171262 MacGregor | U.S. Pat. No. 5035706 Gianturco et al |
| U.S. Pat. No. 5059211 Stack et al | U.S. Pat. No. 5041126 Gianturco |
| U.S. Pat. No. 5104399 Lazarus | U.S. Pat. No. 5061275 Wallsten et al |
| U.S. Pat. No. 5104404 Wolff | U.S. Pat. No. 5064435 Porter |
| U.S. Pat. No. 5019090 Pinchuk | U.S. Pat. No. 5092841 Spears |
| U.S. Pat. No. 4954126 Wallsten | U.S. Pat. No. 5108416 Ryan et al |
| U.S. Pat. No. 4994071 MacGregor | U.S. Pat. No. 4990151 Wallsten |
| U.S. Pat. No. 4580568 Gianturco | U.S. Pat. No. 4990155 Wilkoff |
| U.S. Pat. No. 4969890 Sugita et al | U.S. Pat. No. 5147385 Beck et al |
| U.S. Pat. No. 4795458 Regan | U.S. Pat. No. 5163952 Froix |
| U.S. Pat. No. 4760849 Kropf | |
| U.S. Pat. No. 5192297 Hull | |

In U.S. Pat. No. 5,348,538, incorporated herein by reference, there is described a single layer balloon which follows a stepped compliance curve. The stepped compliance curves of these balloons has a lower pressure segment following a first generally linear profile, a transition region, typically in the 8–14 atm range, during which the balloon rapidly expands yielding inclastically, and a higher pressure region in which the balloon expands along a generally linear, low compliance curve. The stepped compliance curve allows a physician to dilate different sized lesions without using multiple balloon catheters.

Stepped compliance curve catheter balloon devices using two different coextensively mounted balloon portions of different initial inflated diameter, are also described in co-pending U.S. application Ser. No. 08/243,473, filed May 16, 1994 as a continuation of now abandoned U.S. application Ser. No. 07/927,062, filed Aug. 8, 1992, and in U.S. Pat. No. 5,358,487 to Miller. These dual layer balloons are designed with the outer balloon portion larger than the inner portion so that the compliance curve follows the inner balloon portion until it reaches burst diameter and then, after the inner balloon bursts, the outer balloon becomes inflated and can be expanded to a larger diameter than the burst diameter of the inner balloon.

A polyethylene ionomer balloon with a stepped compliance curve is disclosed in EP 540 858. The reference suggests that the balloon can be used on stent delivery catheters. The disclosed balloon material of this reference, however, yields a compliant balloon and therefore a stent delivered with such a balloon would typically require "retouch."

SUMMARY OF THE INVENTION

The invention in one aspect is directed to a method for method for installing a stent in a vessel utilizes a single balloon catheter for both low pressure predilation at a relatively small diameter to open the lesion sufficiently to allow insertion and deployment of the stent across the lesion and for subsequent high pressure embedding of the stent in the vessel wall. The same balloon catheter may also be employed to insert and deploy the stent. Thus at least one catheter may be eliminated from what has heretofore been a two or three catheter installation process. The balloons utilized in the method have a stepped compliance curve which allows for predilation at a low pressure and predetermined diameter and for high pressure embedding at a substantially larger diameter.

In a further aspect of the invention novel balloon structures having high wall strengths, high burst pressures and low compliance are provided in which a first portion of the balloon body has a generally linear compliance curve and a second portion of the balloon body has a stepped compliance curve. Both portions of the balloon are configured to have essentially the same diameter at low pressure so that the entire balloon may be used to predilate a lesion. However at higher pressure the configuration of the balloon changes due to rapid expansion of the second balloon portion. At still higher pressures the compliance curve of the second portion levels off to a low compliance profile so that this portion of the balloon can be used for high pressure embedment of the stent without substantially increasing the stent size. With such balloons, exposure of the vessel wall areas which are not reinforced by the stent to high pressure can be avoided, despite the typically shorter length of conventional stents than the typical length of predilation balloons.

The novel balloons of the invention are made by molding a balloon into a configuration in which the second portion has a larger diameter than the first portion and then shrinking the second portion to the diameter of the first portion. The method of making such balloons comprises yet another aspect of the invention.

These and other aspects and advantages of the present invention will no doubt become apparent to those skilled in the art after having read the following detailed description of the invention as illustrated by the various drawing figures.

DETAILED DESCRIPTION OF THE PREFERRED EMBODIMENT

The catheters employed in the practice of the present invention are most conveniently constructed as over-the-wire balloon catheters of conventional form for use in angioplasty, except that the balloon has a stepped compliance curve. However it should be understood that the present invention can be applied, in addition to over-the-wire catheters, to fixed-wire catheters, to shortened guide wire lumens or single operator exchange catheters, and to non over-the-wire balloon catheters. Furthermore this invention can be used with balloon catheters intended for use in any and all vascular systems or cavities of the body.

Figure 1:
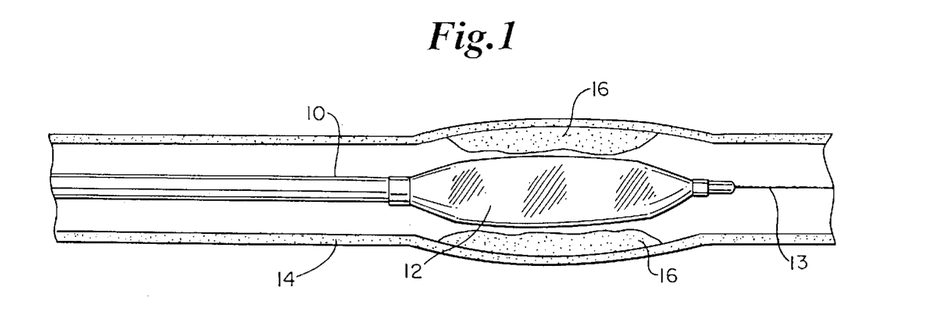
FIG. 1 is a longitudinal sectional view of a vessel showing an angioplasty catheter, not in section and having a stepped compliance curve balloon on the distal end thereof, inserted in the vessel and predilating a lesion in the vessel.

Referring to FIGS. 1–5, the process of the invention is illustrated by these Figures. In FIG. 1, a catheter 10 carrying a balloon 12 on the distal end thereof has been inserted over guide wire 13 into a vessel 14 and fed to a lesion 16 where it is used to predilate the lesion to a predetermined diameter, typically about 2.5 mm. In the process of the invention, balloon 12 is made of a high strength polymer, such as PET and has a stepped compliance curve, the predilation diameter is below the transition region on that curve and the desired final dilated diameter, typically 2.75–4.0 mm, lies on the portion of the curve above the transition region. After the predilation the balloon is deflated and the catheter 10 is removed from the vessel 14.

Figure 2:
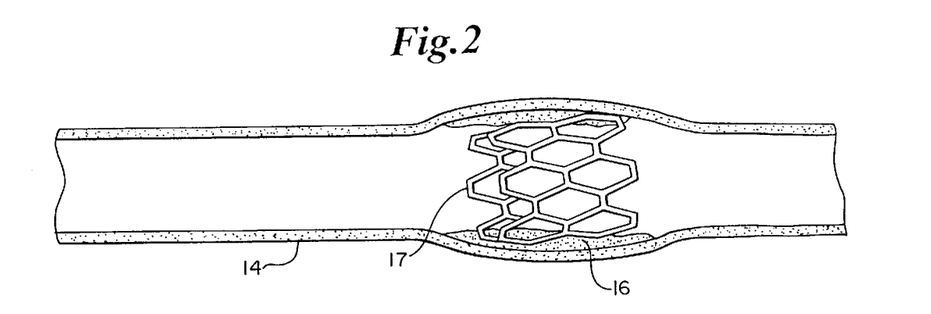
FIG. 2 is a view of a vessel as in FIG. 1 after installation of a stent but before a "retouch" procedure.

The next step is to deliver the stent to the lesion. In a first embodiment of the process, a separate stent delivery catheter of any conventional type is used to deliver the stent to the lesion, install the stent in place across the lesion, and further dilate the lesion to a larger diameter, typically 2.75–4.0 mm. The delivery catheter is then withdrawn to leave the stent 17 in place across the dilated lesion, as shown in FIG. 2. Occasionally as indicated in FIG. 2 the stent is not fully seated or can move somewhat after installation if the installation process is discontinued at this point.

To assure that the stent is firmly seated in the lesion so that it cannot move and to additionally reduce occurances of restenosis and thrombus formation, in this embodiment of the inventive process, after the delivery catheter has been removed, catheter 10 is reinserted and expanded to a retouch pressure, typically above 9 atm and preferably in the range of 12–20 atm.

Figure 3:
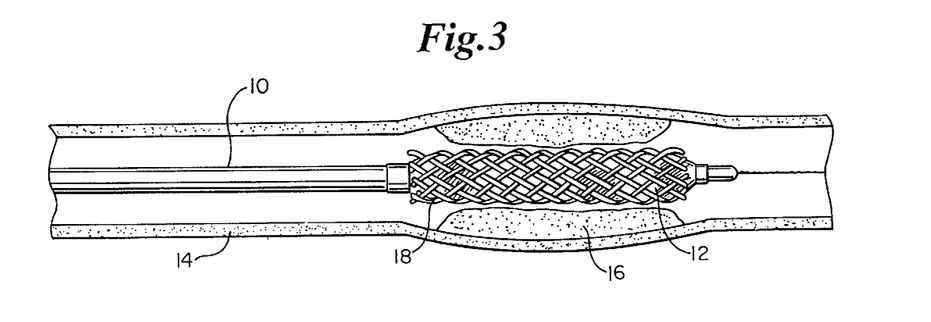
FIG. 3 is a view as in FIG. 1 in which after predilation and with the same catheter, now carrying a stent mounted over the balloon, reinserted to deliver the stent to the lesion.
Figure 4:
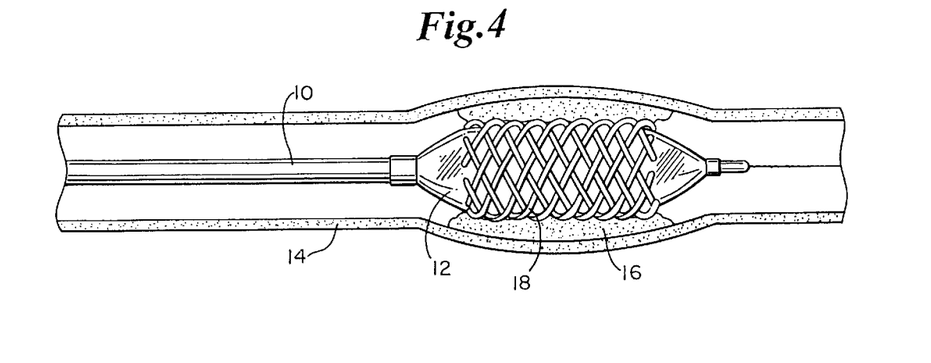
FIG. 4 is a view as in FIG. 3 with the balloon expanded to install the stent and further dilate the lesion.

Alternatively, catheter 10 may be employed as a delivery catheter. In the specific embodiment illustrated in FIGS. 3–4, an unexpanded stent 18 has been mounted on the catheter 10 over balloon 12 after catheter 10 has been used to predilate the lesion and has been removed from the lesion. Catheter 10 is then reinserted into the vessel 14 and located across the lesion (FIG. 3). Balloon 12 is then reinflated as shown in FIG. 4 to expand and install the stent 18 and to dilate the lesion. The pressure employed is one which inflates the balloon to a diameter above the transition region and therefore the same balloon as used in predilation can be used to deliver the catheter and dilate the lesion. Further, because the balloon 12 follows a low compliance curve above the transition region, the pressure can safely be increased above 12 atm so as to firmly seat stent 18 without having to undergo "retouch." Typically the balloon 12 will be capable of inflation to at least as high as 20 atm.

Figure 5:
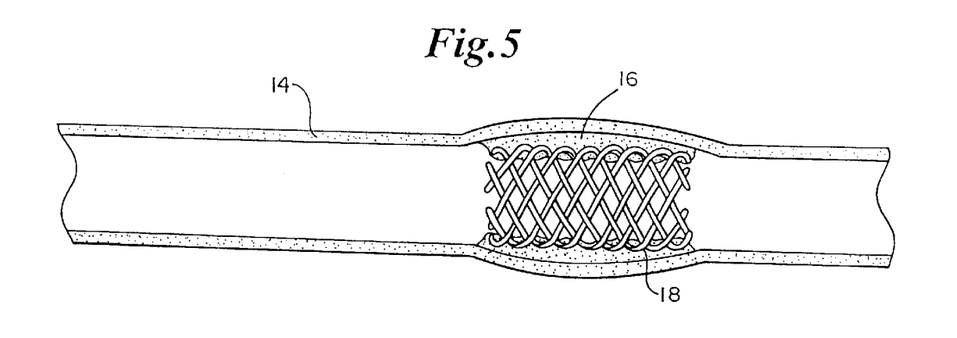
FIG. 5 is a view as in FIG. 3 after completion of the procedure of FIG. 3.

FIG. 5 depicts the stent 18 in place after high pressure dilation. A similar result is obtained if the catheter 10 is used for predilation and for "retouch" but not for stent installation. It should be noted that the specific configuration of the stents 17 and 18 is not critical and two different configurations have been depicted merely to indicate that different configurations may be employed in either embodiment of the inventive installation process. The particular configurations employed may be reversed or another stent configuration, including balloon expandable stents and self-expandable stents, may be substituted without departing from the invention hereof.

Thus unlike the prior art methods for accomplishing the same sequences of predilation, stent delivery/dilation and high pressure seating or "retouch," a separate catheter is not required to be used in the final high pressure seating step from the catheter used in the predilation step. This significantly reduces the cost of the procedure, since the catheter costs are a significant part of the overall cost of the procedure.

The stepped compliance curve balloons should be made of a thermoplastic polymer material which has a high strength, and gives a low compliance balloon at pressures above about 15 atmospheres. For purposes of this application "low compliance" is considered to correspond to a diameter increase of no more than 0.1 mm per increased atmosphere of pressure, preferably less than 0.06 mm/atm. Suitably the balloon polymer is poly(ethylene terephthalate) (PET) of initial intrinsic viscosity of at least 0.5, more preferably 0.7–0.9. Other high strength polyester materials, such as poly(ethylene napthalenedicarboxylate) (PEN), nylons such as nylon 11 or nylon 12, thermoplastic polyimides and high strength engineering thermoplastic polyurethanes such as Isoplast 301 sold by Dow Chemical Co., are considered suitable alternative materials. Desirably the balloon is blown in a way which will give a wall strength of at least 18,000 psi, preferably greater than 20,000 psi. Techniques for manufacturing balloons with such wall strengths are well known.

After being blown, the balloon is provided with a stepped compliance curve by annealing the balloon for a short time after blowing at a pressure at or only slightly above ambient and at a temperature which causes the blown balloon to shrink. The process is described in U.S. Pat. No. 5,348,538. However, the balloons of the invention are desirably constructed with a greater difference between the low pressure and high pressure linear regions of the compliance curve so that the transition between the two regions results in a step-up of diameter of the balloon of at least 0.4 mm. This is accomplished by blowing the balloon to the larger diameter and then shrinking to a greater extent than was done in the specific illustrative examples of U.S. Pat. No. 5,348,538. The amount of shrinkage is controlled by the pressure maintained in the balloon during annealing and the temperature and time of the annealing. For a balloon made from 0.74 intrinsic viscosity PET, the blowing pressure is suitably in the range 200–400 psi, and temperature is suitably in the range of 90–100° C., and the annealing pressure is in the range of 0–20, preferably 5–10 psi at 90–100° C. for 3–10 seconds.

In a further aspect of the invention, the balloons employed in the inventive process are configured so that a first portion of the body of the balloon has a stepped compliance curve and the remainder of the balloon has an unstopped compliance curve, the low pressure regions of the compliance curves of both the first portion and the remainder portion(s) being generally collinear. By this means the length of the balloon which will expand and seat the stent will be smaller than the length which is used to accomplish predilation. Since many stents are in the 7–10 mm length range whereas predilation balloons are desirably 15–20 mm or even longer, this shorter configuration for the portion which will step-up to a larger diameter ("hyper-extend") is desirable so that the hyper-extension will not overlap tissue which is unreinforced by the stent. Two balloons of this preferred configuration are shown, mounted on catheters, in FIGS. 6 and 8.

Figure 6:
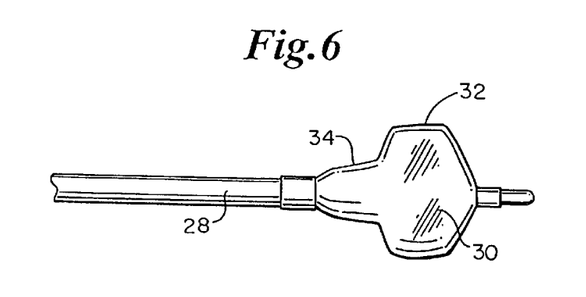
FIG. 6 is a side view the distal end of a catheter having an alternate balloon of the invention, shown in hyperextended form.
Figure 7:
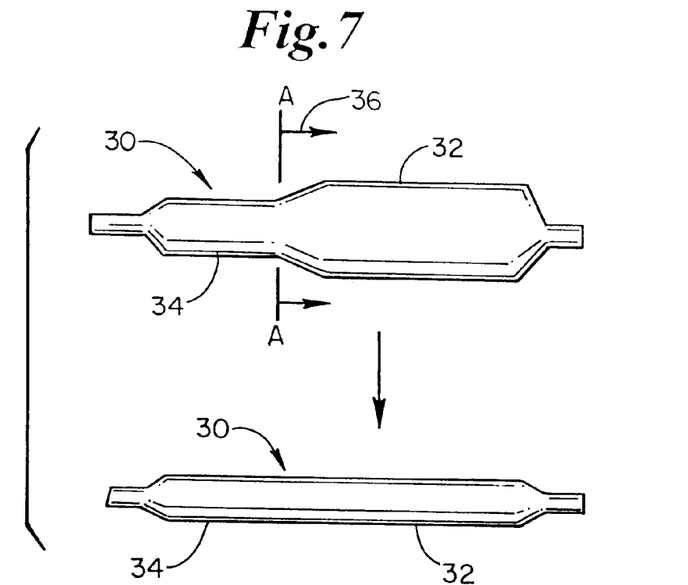
FIG. 7 is a schematic illustration depicting the process stages for preparing a balloon as in FIG. 6.
Figure 11:
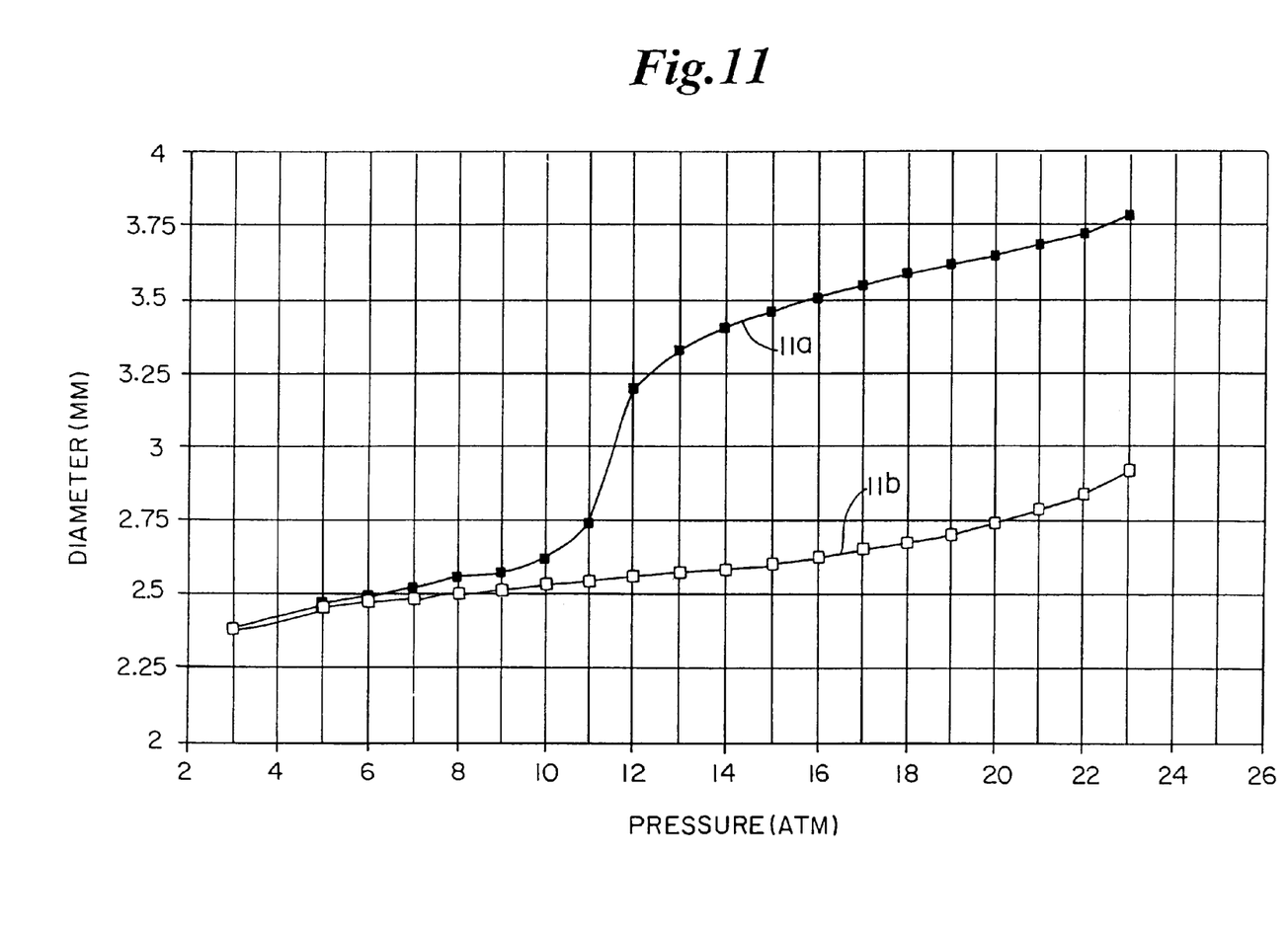
FIG. 11 is a graph of the compliance curves of a balloon of the type shown in FIG. 6.

In FIG. 6, the balloon 30 is shown in its fully expanded high pressure configuration, mounted on a catheter 28. As shown schematically in FIG. 7, this balloon is blown in a mold of the general shape of the balloon in FIG. 6 and then the annealing step is performed on the enlarged portion 32 by dipping the balloon in the direction indicated by arrows 36 to level A in a bath of heated water or other suitable heated fluid while the balloon is pressurized at low pressure, for instance 0–10 psi, so that only portion 32 is annealed. After annealing portion 32 will be shrunken so that, the configuration of the balloon will be substantially linear and will expand generally linearly until pressurized above about 8–12 atm. At higher pressures, the portion 34 of balloon 30 will continue to expand along the same generally linear curve but portion 32 will rapidly expand until the balloon configuration is restored to shape shown in FIG. 6, after which the expansion profile of portion 32 will level out again to a non-compliant curve but at a substantial increase in absolute diameter relative to the diameter of portion 34. Balloons of this configuration, have been used to produce compliance curves as shown in FIG. 11.

It should be understood that while FIG. 6 shows portion 32 of balloon 30 mounted distally on catheter 28, balloon 30 may instead be mounted with portion 34 mounted distally without departing from the invention hereof.

If the balloon of FIG. 6 is used to deliver and install the stent, the catheter 28 will have to be backed up a short distance to center portion 32 under the stent after expansion of balloon 30 sufficiently to bring it into contact with the lesion but before the balloon portion 32 is fully expanded to fully dilate the lesion and set the stent. This can be accomplished by providing marker bands (not shown) on the portion of the catheter shaft under the balloon to indicate the proximal and distal boundries of portion 32.

Figure 8:
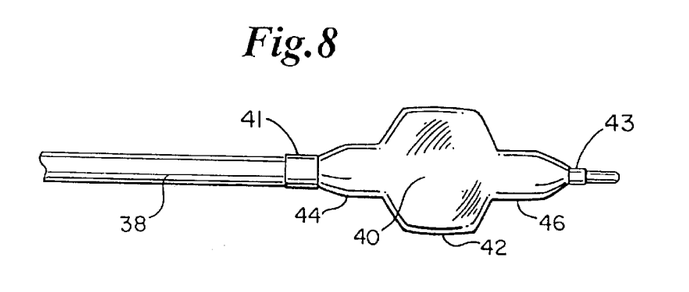
FIG. 8 is a view of a catheter as in FIG. 6 except that a second alternate balloon of the invention is depicted.
Figure 9:
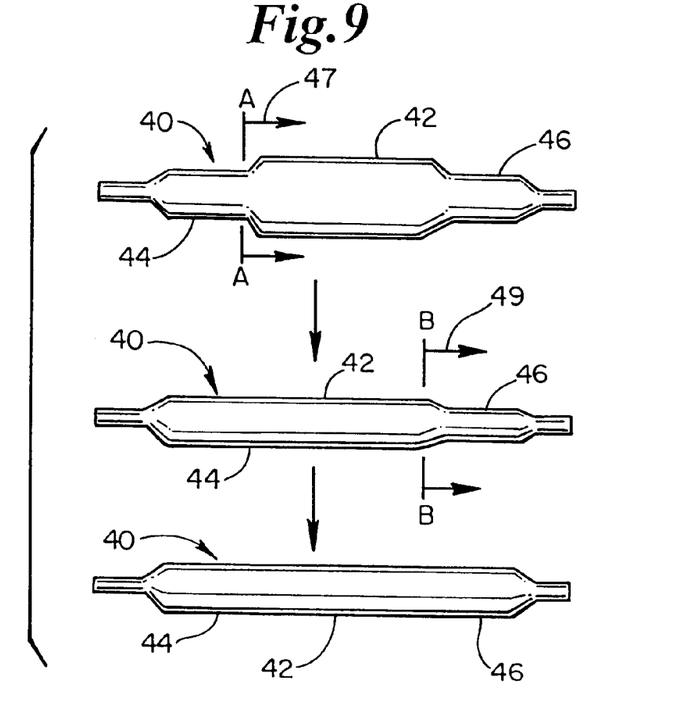
FIG. 9 is a schematic illustration depicting the process stages for preparing a balloon as in FIG. 8.

In the alternate embodiment of FIG. 8, the balloon 40, mounted on catheter 38, has a hyper-extensible portion 42 located centrally on the balloon body. The balloon is mounted on the catheter at balloon end regions 41, 43, located on opposite ends of the balloon body. Therefore, after installation of the stent, the high pressure stent setting step can be performed immediately without repositioning the catheter and without risking damage to tissue unreinforced by the stent. This balloon is blown in a mold having a configuration which is substantially the shape shown in FIG. 8. To anneal and shrink portion 42 to the diameter of portions 44, 46, heating during annealing may be confined to the central portion 42, suitably by heating with a hot air stream, using baffles to protect the end regions 44, 46 from the air stream. Alternatively, as shown schematically in FIG. 9, the balloon 40 is dipped in the direction of arrows 47 to level A in a heated bath to fully immerse portions 42 and 46, until portion 42 has reached the diameter of portion 44. At this point portion 46 will be shrunk to a diameter less than portion 44. Balloon 40 is then dipped into a heated bath in the direction of arrows 49 to level B so that only portion 46 is immersed and then portion 46 is reblown to the diameters of portion 44 and shrunken portion 42. This reblowing step may be accomplished either with the aid of a mold or by free-blowing.

Figure 10:
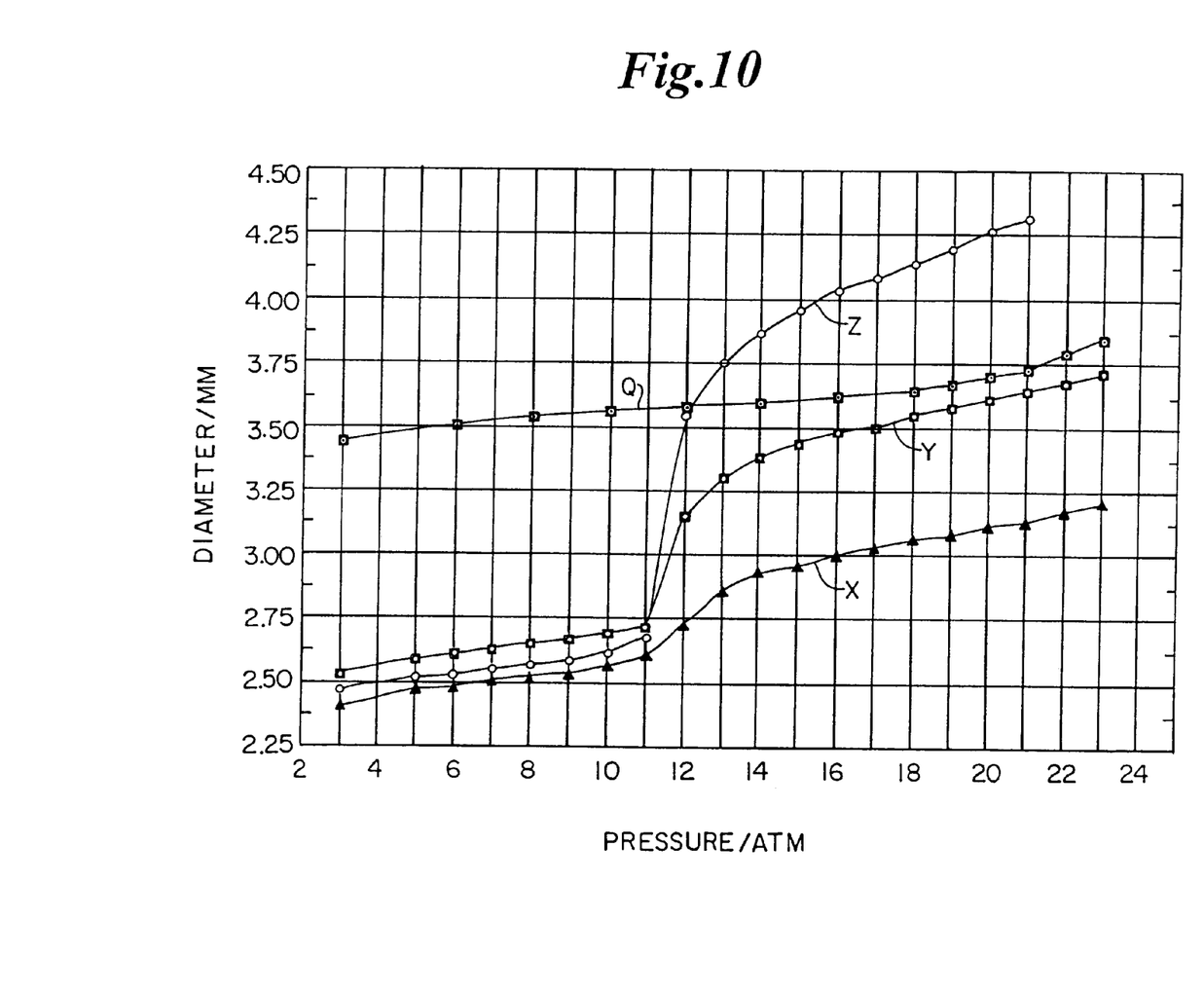
FIG. 10 is a graph showing the compliance curves of several balloons of the type shown in FIGS. 1, 3 and 4 compared to a conventional 3.5 mm angioplasty balloon of the same material.

Referring now to the graph shown in FIG. 10, in which pressure in atmospheres is plotted on the x-axis and balloon diameter in millimeters is plotted on the y-axis. The compliance curves of several balloons have been manufactured in accordance with 5,348,538 and useful in the practice of this invention have been plotted on this graph and compared to a conventional 3.5 mm angioplasty balloon Q of the same PET material. The stepped compliance curve balloons, X, Y and Z, plotted on this graph had nominal diameters prior to being, shrunk of 3.0, 3.5 and 4.0 millimeters, respectively.

FIG. 11 is a graph of the compliance curves of a balloon of the type shown as balloon 30 in FIG. 6. Curve 11a is the compliance curve of portion 32 of balloon 30 and curve 11b is the compliance curve of the portion 34 of balloon 30. The balloon was made from PET of 0.74 intrinsic viscosity and, after blowing had a body wall thickness of 0.0013 inches. Portion 32 thereof was annealed by dipping in a 95° C. water bath for 5 seconds, while pressurized at 10 atm pressure, to shrink portion 32 to the diameter of portion 34. The balloon was then mounted on a catheter and the compliance curve obtained by incrementally inflating the balloon until burst, measuring the diameter of both portions 32 and 34 at each incremental pressure.

With regard to definitions, FIG. 11 can be referred to for illustration of what is meant by "generally linear" with reference to the portions of curve 11a between 3 and 10 atm and again between about 13 and 26 atm. Curve 11b is considered generally linear through out its entire length. "Generally collinear" is considered to encompass divergences between two curves of no more than about 0.2 atm, preferably less than 0.15 mm divergence between the two curves. Curves 11a and 11b are "generally collinear" in the range from 3 atm to about 10 atm.

The invention may also be practiced by use of dual layer balloons such as described in co-pending U.S. application Ser. No. 08/243,473, filed May 16, 1994 now U.S. Pat. No. 5,447,497 as a continuation of now abandoned U.S. application Ser. No. 07/927,062, filed Aug. 8, 1992, incorporated herein by reference, and in U.S. Pat. No. 5,358,487, incorporated herein by reference. Suitably both balloons of the dual layer balloons are low compliance balloons designed with the outer balloon portion larger by at least 0.25 mm than the inner portion and the inner balloon designed to burst at a pressure below about 15 atm so that the compliance curve follows the inner balloon portion until it reaches burst diameter and then, after the inner balloon bursts, the outer balloon becomes inflated and can be expanded to a larger diameter than the burst diameter of the inner balloon.

Although the present invention has been described in terms of specific embodiments, it is anticipated that alterations and modifications thereof will no doubt be come apparent to those skilled in the art. It is therefore intended that the following claims be interpreted as covering all such alterations and modifications as fall within the true spirit and scope of the invention.

I claim:

1. A mold for a catheter balloon, the mold having a configuration providing sequentially adjacent first, second and third body portions of the balloon located between first and second cylindrical balloon end regions, each body portion, and each said end region, having a respective diameter, the body portion diameters being greater than the end region diameters and the second body portion diameter being greater than the first and third body portion diameters.

2. A mold as in claim 1 wherein the diameters of the balloon first and third body portions are substantially equal.

* * * * *